US006395875B1

(12) United States Patent
Freimuth (10) Patent No.: US 6,395,875 B1
(45) Date of Patent: May 28, 2002

(54) RECOMBINANT SOLUBLE ADENOVIRUS RECEPTOR

(75) Inventor: Paul I. Freimuth, East Setauket, NY (US)

(73) Assignee: Brookhaven Science Associates LLC, Upton, NY (US)

( * ) Notice: Subject to any disclaimer, the term of this patent is extended or adjusted under 35 U.S.C. 154(b) by 0 days.

(21) Appl. No.: 09/236,423

(22) Filed: Jan. 25, 1999

(51) Int. Cl.[7] ............................................. C07K 14/705
(52) U.S. Cl. ...................... 530/324; 530/326; 530/350
(58) Field of Search ................................ 530/350, 326, 530/324

(56) References Cited

PUBLICATIONS

Freimuth, P., *J. Virol. 70:* 4081–4085 (1996).
Bork et al., *J. Mol. Biol. 242:* 309–320 (1994).
Tomko et al., *Proc. Natl. Acad. Sci. USA 94:* 3352–3356 (1997).
Lonberg–Holm et al., *Nature 259:* 679–681 (1976).
Defer et al., *J. Virol. 64:* 3661–3673 (1990).
Xia et al., *Structure. 2:* 1259–1270 (1994).
Mayr and Freimuth, *J. Virol. 71:* 412–418 (1997).
Bergelson et al., *Science 275:* 1320–1323 (1997).

*Primary Examiner*—David Guzo
(74) *Attorney, Agent, or Firm*—Margaret C. Bogosian

(57) ABSTRACT

Disclosed are isolated polypeptides from human CAR (coxsackievirus and adenovirus receptor) protein which bind adenovirus. Specifically disclosed are amino acid sequences which corresponds to adenovirus binding domain D1 and the entire extracellular domain of human CAR protein comprising D1 and D2. In other aspects, the disclosure relates to nucleic acid sequences encoding these domains as well as expression vectors which encode the domains and bacterial cells containing such vectors. Also disclosed is an isolated fusion protein comprised of the D1 polypeptide sequence fused to a polypeptide sequence which facilitates folding of D1 into a functional, soluble domain when expressed in bacteria. The functional D1 domain finds application for example in a therapeutic method for treating a patient infected with a virus which binds to D1, and also in a method for identifying an antiviral compound which interferes with viral attachment. Also included is a method for specifically targeting a cell for infection by a virus which binds to D1.

6 Claims, 4 Drawing Sheets

Adeno Knob STEM MW
n=839 mean=60.6

SEQUENCE LISTING

<160> NUMBER OF SEQ ID NOS: 9

<210> SEQ ID NO 1
<211> LENGTH: 22
<212> TYPE: PRT
<213> ORGANISM: Artificial Sequence
<220> FEATURE:
<223> OTHER INFORMATION: Description of Artificial Sequence: CLONING
      VECTOR ENCODED SEQUENCES

<400> SEQUENCE: 1

Leu Glu Asp Pro Ala Ala Asn Lys Ala Arg Lys Glu Ala Glu Leu Ala
 1               5                  10                  15

Ala Ala Thr Ala Glu Gln
            20

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: CLONING
      PRIMER

<400> SEQUENCE: 2
catatgagca acactccata cg                                           22

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: CLONING
      PRIMER

<400> SEQUENCE: 3
ggatccttat tcttgggtaa tgt                                          23

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence: CLONING
      PRIMER

<400> SEQUENCE: 4
ccatgggtat cactactcct gaagaga                                      27

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: CLONING
      PRIMER

<400> SEQUENCE: 5
ctcgagcgca cctgaaggct ta                                           22

<210> SEQ ID NO 6
<211> LENGTH: 21
<212> TYPE: DNA
<213> ORGANISM: Artificial Sequence
<220> FEATURE:

```
<223> OTHER INFORMATION: Description of Artificial Sequence: CLONING
      PRIMER

<400> SEQUENCE: 6
ctcgagtgaa ggagggacaa c                                            21

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: CLONING
      PRIMER

<400> SEQUENCE: 7
catatgggta tcactactc                                               19

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: CLONING
      PRIMER

<400> SEQUENCE: 8
ggatcctacg cacctgaagg ct                                           22

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: CLONING
      PRIMER

<400> SEQUENCE: 9
ggatcctatc cagctttatt tgaag                                        25
```

RECOMBINANT SOLUBLE ADENOVIRUS RECEPTOR

This invention was made with Government support under contract number DE-AC02-98CH10886, awarded by the U.S. Department of Energy. The Government has certain rights in the invention.

BACKGROUND OF THE INVENTION

Characterization of the molecular basis for virus attachment to cells has importance both for understanding virus tropism and for developing agents that inhibit virus binding or alter the specificity of binding. Recently, a 10 cellular receptor for adenovirus type 2 and other closely related serotypes was identified. This receptor, encoded by a single gene on human chromosome 21 (Mayr et al., *J. Virol.* 71: 412–8 (1997)), is a 46 kD glycoprotein which also serves as a receptor for group B coxsackieviruses (CBV) and thus was termed CAR. CAR mRNA is present in varying abundance in many human tissues. A broad tissue distribution of CAR protein expression correlates with the broad tropism of CBV, but subgroup C adenoviruses that are known to bind CAR have a much more restricted tropism limited primarily to the upper respiratory tract. Thus, other factors in addition to receptor availability clearly have important roles in determining adenovirus tropism. Although adenovirus binds to CAR with high affinity (Mayr et al., *J. Virol.* 71: 412–8 (1997); Wickham et al., *Cell.* 73: 309–19 (1993)), virus titers are significantly reduced on cells with down-regulated CAR expression (Freimuth, P., *J. Virol.* 70: 4081–5 (1996)). These results suggest that adenovirus infection in vivo may be restricted to cells which express CAR at levels above a minimum threshold concentration. CAR protein levels are relatively low on the apical surface of differentiated (ciliated) respiratory epithelial cell cultures, which may account for the poor efficiency of Gadenoviral gene transfer to human lung tissue in vivo.

Adenovirus binding to CAR results from an interaction between rod-shaped proteins located at the capsid vertices, called viral fibers, and the extracellular region of CAR. The distal, carboxy-terminal end of fiber consists of a globular domain, termed the knob, which has receptor-binding activity. The knob domain of adenovirus type 5 (Ad5) was expressed in *E. coli* as a soluble, trimeric, biologically active protein, and its 3-dimensional structure was determined by x-ray crystallography. The predicted amino acid sequence of CAR suggests a structure consisting of two extracellular domains related to the immunoglobulin IgV and IgC2 domain folds (Bork et al., *J. Mol Biol.* 242: 309–20 (1994); Bergelson et al., *Science* 275: 1320–3 (1997); Tomko et al., *Proc. Natl. Acad. Sci. USA* 94: 3352–6 (1997)), a single membrane-spanning region, and one carboxy-terminal cytoplasmic domain. Regions of CAR necessary for binding the fiber knob domain have not yet been determined.

SUMMARY OF THE INVENTION

In one aspect, the present invention relates to an isolated polypeptide comprising an amino acid sequence which corresponds to adenovirus binding domain D1 of human CAR (coxsackievirus and adenovirus receptor) protein. The present invention also relates to an isolated polypeptide comprising an amino acid sequence which corresponds to extracellular domains D1 and D2 of human CAR protein, which also demonstrates adenovirus binding activity. In other aspects, the invention relates to nucleic acid sequences encoding the D1 and combined D1 and D2 domains. The invention also relates to expression vectors which encode the domains as well as bacterial cells containing such vectors. In a preferred embodiment the D1 polypeptide sequence is fused to a polypeptide sequence which facilitates folding of D1 into a functional, soluble domain when expressed in bacteria.

In another embodiment, the invention relates to a therapeutic method for treating a patient infected with a virus which binds to D1, such as adenoviruses from subgroups A and C, or coxsackievirus subgroup B. The method involves providing a therapeutic composition comprising. D1 and administering it to a patient. Administration is generally topical and to a localized region. Areas of localized infection suitable for treatment include the ocular region, the upper respiratory tract and the gastrointestinal region.

Also encompassed within the scope of the invention are methods based on the experiments described in the Exemplification section set forth below. These include, for example, methods for identifying a protein, and its binding domain, which binds D1, and also a method for identifying an antiviral compound which interferes with viral attachment. Also included is a method for specifically targeting a cell for infection by a virus which binds to D1. This method has practical use in gene therapy, which often utilizes adenovirus expression vectors.

BRIEF DESCRIPTION OF THE DRAWINGS

FIG. 1 (Parts A–C) is a diagrammatic representation of the Ad12 fiber knob and the extracellular domains of human CAR. a) The Ad12 knob domain (solid line) begins at a conserved motif (amino acids 409–412) and extends to the fiber protein carboxy terminus (Glu 587) (corresponding to nucleotides 30592–31128 of GenBank Accession #X73487). A fragment of Ad12 DNA encoding the entire knob domain and several amino acids from the preceding fiber shaft region (hatched box) was amplified by PCR using forward primer #1 and reverse primer #2. The resulting PCR product was cloned between the NdeI and BamHI sites of pET15b. b) The human CAR protein consists of a N-terminal signal peptide (open box), two extracellular Ig-related domains (D1, D2), a membrane spanning region (TM) and a cytoplasmic domain (CYT). CDNA fragments encoding D1 and D1/D2 were amplified by PCR using forward primer #3 and reverse primers #4 and #5. The resulting PCR products were cloned between the NcoI and XhoI sites of pET20b. Similar D1- and D1/D2-encoding cDNA fragments were amplified by PCR using forward primer #6 and reverse primers #7 and #8. The resulting PCR products were cloned between the NdeI and BamHI sites of pET15b. The NcoI-XhoI fragments were transferred from pET20b into pET15b, a manipulation which resulted in the fusion of the genes in frame to pET15b vector DNA encoding a 22 amino acid extension at the carboxy-terminus. c) pET vectors for protein expression in *E. coli*. The open and filled boxes represent bacterial signal peptides and hexahistidine tags, respectively. The restriction sites used in this study are shown, and the sequence of the pET15b-encoded 22 amino acid carboxy-terminal extension of sD1 is indicated in single letter code (SEQ ID NO:1).

DETAILED DESCRIPTION OF THE INVENTION

The present invention is based, in one aspect, on the discovery that the adenovirus-binding activity of human CAR is localized in the amino-terminal IgV-related domain. As detailed in the Exemplification section, the isolated amino-terminal IgV-related domain of CAR (referred to herein as D1) and the entire extracellular region (referred to herein as D1/D2) both have the ability to form complexes with Ad12 knob. Furthermore, the presence of free D1 in soluble form, inhibits Ad2 virus infection of HeLa cells. Collectively, these observations indicate that D1 is the component of CAR responsible for the adenovirus-binding activity.

One embodiment of the present invention is an isolated polypeptide that binds adenovirus comprising an amino acid sequence corresponding to the D1 domain of the human CAR protein. The preferred embodiment is an isolated polypeptide comprising residues 20–144 of the pre-CAR sequence (GenBank Accession #Y07593), with the amino acid substitutions of L20M and S21G, generated to facilitate cloning. The wild type sequence comprising residues 20–144 of pre-CAR also binds adenovirus, as does a polypeptide sequence comprising residues 20–144 of the pre-CAR sequence which contains one or more conservative amino acid substitutions.

Another embodiment of the present invention is an isolated polypeptide comprising an amino acid sequence corresponding to the D1 and D2 domains of the human CAR protein. D1 and D2 are IgV and IgC2 domains and constitute the entire extracellular region of the human CAR protein. The D1/D2 polypeptide demonstrates analogous viral binding activity to the D1 polypeptide described above. The preferred embodiment comprises the amino acid sequence corresponding to residues 20–237 of the human pre-CAR protein (GenBank Accession #Y07593), with two amino acid substitutions of L20M and S21G, generated to facilitate cloning. The wild type sequence comprising residues 20–237 of pre-CAR also binds adenovirus, as does a polypeptide sequence comprising residues 20–237 of the pre-CAR sequence which contains one or more conservative amino acid substitutions.

Another aspect of the present invention is the recombinant DNA molecule that encodes the above described polypeptides. One embodiment is a recombinant DNA molecule comprising a DNA sequence encoding the adenovirus binding domain, D1, of the CAR protein. In the preferred embodiment, this sequence corresponds to nucleotide 121 to 493 of the human CAR cDNA (GenBank Accession #Y07593). Another embodiment is the recombinant DNA molecule comprising the entire extracellular region, D1 and D2, of the CAR protein. In the preferred embodiment, this DNA sequence corresponds to nucleotide 121 to 770 of the human CAR cDNA sequence (GenBank Accession #Y07593).

The isolated polypeptides of the present invention can be produced in vitro by inserting the corresponding recombinant DNA molecules described above into an expression vector (e.g. a prokaryotic or eukaryotic expression vector). Such vectors contain all necessary regulatory signals to promote the expression of a DNA sequence of interest. The use of such vectors is a matter of routine experimentation for one of average skill in the art. The expression vector with the inserted DNA sequence of the present invention is then introduced into an appropriate cell under conditions favorable for expression. In the preferred embodiment, the cell is prokaryotic and is a bacteria cell. However, the proteins can also be expressed in eukaryotic cells by similar methods, utilizing eukaryotic expression vectors. Such cells can be used to study the biological properties of the protein in a controlled cell system or, alternatively, for the purpose of protein production and purification.

Isolation of the above proteins from the bacteria is achieved through routine purification procedures. In one embodiment, the CAR coding sequences are engineered downstream of sequences encoding hexahistidine, to produce the CAR fragment with an N-terminal hexahistidine tag. As described in the Exemplification section of this application, the D1 and D1/D2 polypeptides produced by this method are insoluble when generated in $E.\ coli$. However, functional products are obtained when the polypeptides are refolded from urea-solubilized inclusion bodies and purified by anion exchange chromatography. Following purification, the tag is optionally cleaved off by digestion with thrombin to yield the intact CAR fragment.

In the preferred embodiment, the D1 polypeptide is expressed in the form of a fusion protein which results in the production of D1 domain that is soluble and functional when exogenously expressed in $E.\ coli$ at 18° C. As described in the Exemplification section of the present application, D1 engineered to have a short C-terminal amino acid extension is partially soluble when expressed in $E.\ coli$, and also retains virus binding activity. Without being bound by theory, the fused extension is thought to enable the IgV domain to fold into a soluble structure within $E.\ coli$ cells. Functional D1 isolated in this manner is preferred for use over D1 which is produced as insoluble in $E.\ coli$ and resolubilized because resolubilized proteins can contain non-functional structural isomers.

The fusion protein is generated by expression from a recombinant DNA molecule containing the D1 polypeptide coding sequence, described above, fused in frame to a DNA sequence encoding a polypeptide sequence which facilitates folding of the D1 polypeptide into a functional, soluble domain. This recombinant DNA molecule is then inserted into a prokaryotic expression vector which is then transformed into a bacteria cell, under conditions appropriate for expression. In one embodiment the fusion is downstream, resulting in a C-terminal extension. In the preferred embodiment, the D1 coding sequence is fused in frame to a downstream DNA sequence encoding the 22 residue polypeptide LEDPAANKARKEAELAAATAEQ (SEQ ID NO:1) to generate a C-terminal extension. The isolated polypeptide that results from expression of this fused sequence comprises an amino acid sequence corresponding to amino acids 20–144 of human pre-CAR protein, and is herein referred to as sD1.

The present invention is also based, in part, on the discovery that free sD1 polypeptide functions as an antiviral agent by inhibiting viral infection of a cell. Results presented in the Exemplification section of this application indicate that free sD1 functions to inhibit cell infection by viruses that bind D1 of human CAR. As detailed in the Exemplification, both Ad 2 and Ad 12 (representative of adenovirus subgroup C and A, respectively) bind D1. These results, combined with the earlier observation that adenovirus competes for cell binding sites with a subgroup B coxsackievirus, indicate that members of coxsackievirus subgroup B also bind D1 (Lonberg-Holm et al., *Nature* 259: 679–81 (1976); Bergelson et al., *Science* 275: 1320–3 (1997); Tomko et al., *Proc. Natl. Acad. Sci. USA* 94: 3352–6 (1997)).

One embodiment of the present invention is a method for the treatment of a patient infected with a virus characterized as binding D1 of human CAR protein. The method comprises providing a therapeutic composition of D1 polypeptide and administering it to the host. This method can be used to treat any viral infection involving a viral agent that binds to D1 including, but not limited to, adenovirus subgroup A, adenovirus subgroup C, and coxsackievirus subgroup B.

Effective therapeutic compositions will provide a sufficient amount of D1 polypeptide to affect binding of the virus to the extent that progression or spread of the infection is inhibited. In the preferred embodiment, the therapeutic composition comprises the D1 polypeptide in a stable, soluble form. For effective therapy, administration of the composition is targeted to the infected area, preferably through topical administration to a localized infection. Adenoviruses commonly infect the upper respiratory tract, the ocular region, and the gastro-intestinal tract, whereas CBV has a broad tissue tropism. A therapeutic composition may take the form of eyedrops, an inhalant fluid, or an ingestible composition, for the treatment of an ocular, upper respiratory, or gastro-intestinal infection, respectively.

The present invention also encompasses several other methods that utilize the above described compositions. In addition to using D1 polypeptide directly in the therapeutic treatment of viral infection, the isolated polypeptide can be exploited experimentally to identify and characterize molecules which bind CAR through the D1 domain, to study the infection process, and to develop new therapeutics. One such embodiment is a method of identifying molecules and portions thereof involved in binding to CAR through the D1domain.

Experiments presented in the Exemplification section of this application indicate that CAR is bound by adenovirus-encoded proteins involved in cellular attachment. Evidence indicates that other viruses also bind CAR at the D1 domain in the infection process. In addition to this role as a receptor in viral infection, CAR is likely bound by a natural ligand in a healthy individual. Identification of D1 as the domain through which viruses attach to CAR, allows its use in binding assays in the identification and further characterization of these molecules.

Various binding assays can be used to identify and characterize D1 binding molecules. In vitro binding assays yield highly quantitative binding data, and have the advantage of being performed under extremely controlled conditions. In vivo binding assays are performed under physiological conditions and, while often more qualitative than quantitative, can provide physiologically relevant data.

In one embodiment, the molecule which binds D1 is an adenovirus knob protein. Presumably, the residues. of knob that form the interface with CAR are conserved in adenovirus serotypes which bind to CAR, and different in serotypes which do not. The Ad2, representative of subgroup C, and Ad12, representative of subgroup A, knob amino acid sequences are only 43% identical, yet both viruses use CAR as the major attachment receptor. The importance of these conserved amino acids to CAR binding are readily testable using the polypeptide sequences disclosed in the present application. Along the same lines, evidence indicates that subgroup B adenovirus (e.g. types 3 and 7) do not bind the same cell receptors as subgroup A and C (Defer et al., *J Virol*. 64: 3661–73 (1990)): Regions of subgroup B and C knob sequences that differ radically may define receptor binding specificity (Xia et al., *Structure*. 2: 1259–70 (1994)).

In the preferred embodiment, an in vitro binding assay system is used to determine if alterations in viral knob proteins affect binding to D1 or D1/D2 polypeptides. These alterations include truncations and internal deletions of D1 binding knob proteins. Additionally, chimeras of D1 binding and non-D1 binding knob proteins can be tested for D1 binding, to determine the influence of defined knob protein regions on binding specificity. As experiments progress, subtle alterations made in the identified binding regions (e.g. amino acid substitutions) will define the residues involved in D1 binding. One of average skill in the art will recognize that the results of such studies can be applied to the production of recombinant adenovirus knob proteins and/or D1 proteins that possess distinct binding specificities.

Identification of D1 as the virus binding fragment also facilitates structural determination of the virus attachment proteins (e.g. Ad 12 knob, complexed to D1 or D1/D2). Such studies facilitate the identification of residues that form the receptor-knob interface.

The methods used in the study of knob binding are equally applicable to identifying molecules and portions thereof involved in the attachment of viruses other than adenovirus (e.g. coxsackievirus and natural ligands to CAR). One of skill in the art will recognize that information gathered from binding studies will usefully contribute to related applications of the present invention.

The compositions of the present invention can also be used in binding assays to screen for antiviral compounds which interfere specifically with the interaction between the D1 polypeptide of the human CAR protein and a viral attachment protein which binds to the D1 polypeptide. The demonstrated binding of D1 to viral attachment proteins, as detailed in the Exemplification, can be used as an assay for a primary step in virus infection. Compounds found to interfere with viral binding will have valuable therapeutic and experimental potential as antiviral agents.

In one embodiment, purified viral attachment protein is contacted with purified sD1 in an in vitro binding assay (e.g. ELISA type) in the presence and absence of a candidate compound. Decreased binding of D1 to the viral protein indicates the compound possesses anti-viral properties. Both in vitro and in vivo binding assays utilizing various detection methods can be used in such a screen. The performance of such binding assays is within the capabilities of one of average skill in the art. In the preferred embodiment, the viral attachment protein used in the screen is an adenovirus knob protein (e.g. Ad2 or Ad12).

The present invention also provides methods to specifically target a cell for viral infection by redirecting viral binding to a predetermined surface protein of the targeted cell. This can be accomplished by using a D1 containing adaptor bridge which binds to the virus and also binds to the surface protein. Because adenovirus infection in vivo is restricted to cells which express CAR at levels above a minimum threshold concentration, the use of a highly expressed surface protein is expected to produce a higher rate of infection of the target cell than will a less prevalent surface protein. In one embodiment, the adaptor bridge is generated by fusing D1 to single chain antibodies directed towards antigens expressed on the target cells (e.g. tumor cells). The virus is then contacted with the adaptor bridge under conditions appropriate for binding of the virus to the D1 portion of the adaptor bridge, to produce a virus-adaptor bridge complex. The target cell is then contacted with the virus-adaptor bridge complex under conditions appropriate for binding of the antibody portion of the adaptor bridge to the target cell. Contact of the virus-adaptor bridge complex with the target cell can take place via topical application or systemic administration. Upon binding of the virus-adaptor bridge complex to the target protein, the target cell becomes susceptible to infection by the attached virus. In one embodiment, the virus is an adenovirus. However, the virus can be any virus that binds D1, including a virus modified for therapeutic purposes (e.g. by recombinant engineering).

Adenovirus-based DNA expression vectors and delivery systems are highly utilized systems for gene delivery into animal cells, including in vitro cell culture and in vivo delivery (e.g. gene therapy). The use of specific targeting of adenoviruses allows the development of either a wider spectrum of target cells or conversely a narrower range of delivery, the latter improvement being beneficial to therapies such as chemotherapy aimed at specific elimination of diseased tissue. One skilled in the art can envision how information gathered in the above experiments regarding the binding sites involved in Adenovirus binding to D1 can be exploited for therapeutic purposes to generate recombinant adenovirus and D1 with highly specific binding recognition.

The present invention also provides methods for treating a patient with an infection caused by a virus that binds to human CAR. Experiments detailed in the Exemplification indicate that free Ad12 knob inhibits infection of HeLa cells by Ad2 virus. These observations indicate that free adenovirus Ad12 knob protein administered in a therapeutic composition can prevent the spread of an infection resulting from a virus that binds D1. The preparation and administration of effective therapeutic compositions comprising the Ad 12 knob protein are similar to that described above for D1.

EXEMPLIFICATION

Expression and Purification of CAR Extracellular Fragments

To localize the Ad-binding activity of CAR, fragments corresponding the amino-terminal CAR IgV domain (D1) and the combined IgV+IgC2 domains (D1/D2) were expressed in *E. coli*. A cDNA fragment coding for D1 (FIG. 1b) was cloned into pET20b, an expression vector designed to export expressed proteins into the *E. coli* periplasmic space (FIG. 1c), but synthesis of D1 (expected molecular weight of about 16 kDa) was undetectable after 3 hours of induction. No bands corresponding to D1 were detected by SDS-PAGE analysis of whole cell lysates. When the initial construct was enlarged to include the downstream IgC2 domain (FIG. 1b), however, the resulting D1/D2 polypeptide was overexpressed and ran as a closely-spaced doublet on SDS-PAGE, which is characteristic of some periplasmic proteins such as alkaline phosphatase and results from partial hydrolysis of the signal peptide. These results imply that the amino-terminal domain (D1) specified by the initial construct also entered the secretory pathway, but probably was rapidly degraded in the periplasmic space. The D1/D2 protein fragment was not soluble in *E. coli* cells grown at temperatures ranging from 18–37° C.

Figure 1A:
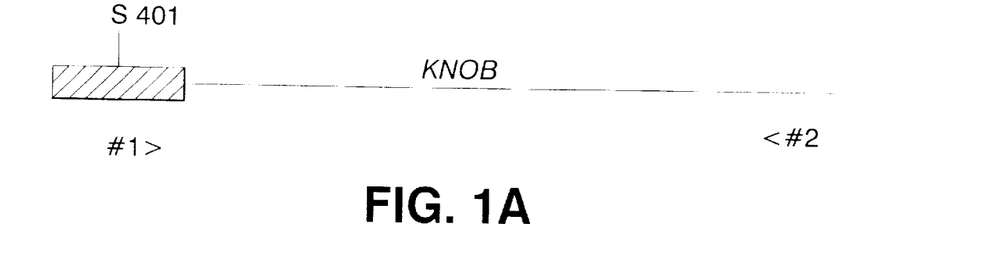
Figure 1B:
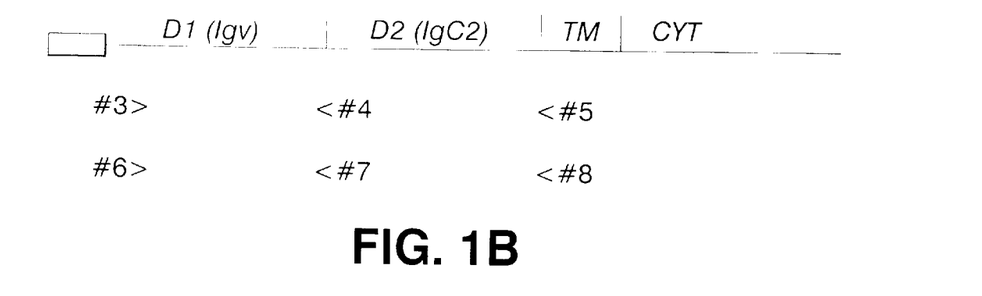
Figure 1C:
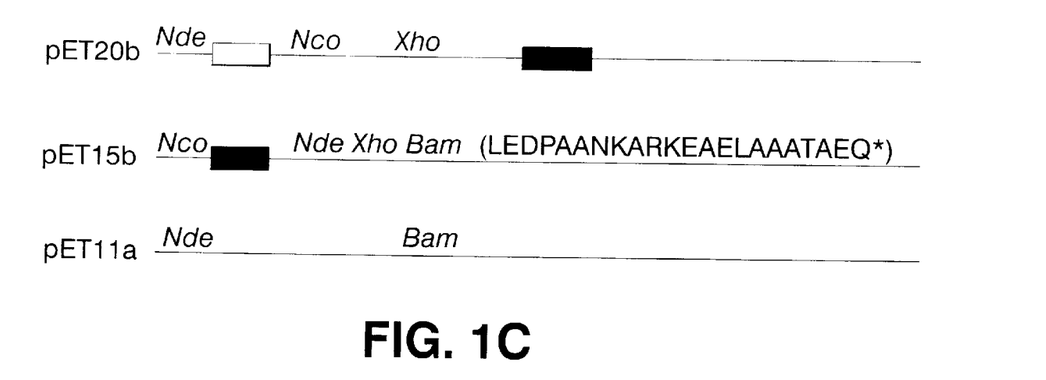

To determine if D1 could be stabilized by restricting its synthesis to the cytoplasm, the D1-encoding PCR product was transferred as a NcoI-XhoI restriction fragment from pET20b into pET15b (FIG. 1c). Because of restriction site differences between these 2 expression vectors, the CAR protein fragment specified by this construct (pET15b-sD1) had a vector-encoded 22-amino acid carboxy-terminal extension and it lacked the amino-terminal hexahistidine tag that is normally attached to proteins expressed from pET15b (FIG. 1c). The resulting polypeptide was expressed at moderate abundance at 37° C., but was insoluble. When the cultures were induced at 18° C., however, a significant amount of D1 was contained in the soluble fraction of cell lysates. SDS-PAGE of the lysate and fractions revealed a band corresponding to the 16 kDa molecular weight of D1 present in all fractions. The larger CAR cDNA fragment encoding D1/D2 also was transferred from pET20b into pET15b, but none of the expressed protein was detected in the soluble fraction of cell lysates. SDS-PAGE analysis of cell lysate and fractions revealed bands corresponding to the molecular weight of about 27 kDa in both the whole cell lysate and insoluble fraction, but absent in the soluble fraction. Soluble D1 (sD1) was partially purified by ammonium sulfate precipitation and ion-exchange chromatography.

To determine if removal of the vector-encoded carboxy-terminal extension would increase the yields of soluble CAR fragments produced in *E. coli*, cDNA fragments encoding D1 and D1/D2 were amplified with new primer sets (primers 6–8, FIG. 1b) that introduced downstream stop codons and also fused the proteins to the vector-encoded amino-terminal hexahistidine tag. Both CAR fragments were overexpressed, but were insoluble at culture growth temperatures between 18–37° C., suggesting that the carboxy-terminal extension sspecified by the initial pET15b-sD1 construct may enable the IgV domain to fold into a soluble structure within *E. coli* cells. The insoluble his-tagged CAR fragments were both refolded from urea-solubilized inclusion bodies and were purified to apparent homogeneity by anion exchange chromatography. To confirm that D1 solubility within intact *E. coli* cells depends on the presence of the 22 amino acid C-terminal extension rather than the absence of the N-terminal hexahistidine leader, the D1-encoding insert (PCR product of primers #6 and #7, FIG. 1b) was transferred from pET15b into pET11a as an NdeI-BamHI fragment (FIG. 1c). D1 was overexpressed in pET11a-D1-transformed cells, but was completely insoluble, as determined by comparison of whole cell lysate to soluble cell fractions by SDS-PAGE analysis, confirming that the C-terminal 22 amino acid extension specified by pET15b increases D1 solubility.

Biological Activity of CAR Extracellular Fragments

Refolded D1 and D1/D2 CAR fragments were examined for the ability to form specific complexes with recombinant fiber knob from Ad12. It was previously reported that infection of HeLa cells by Ad12 virus is inhibited by purified native fiber protein from Ad2, suggesting that CAR serves as the major attachment receptor for both Ad2 and Ad12. A fragment of Ad12 DNA coding for the fiber knob domain (FIG. 1a) was cloned in pET15b. Ad12 knob was abundantly expressed following IPTG induction of cultures at 37° C., but accumulated entirely within the insoluble fraction of cell lysates. When cultures were induced at 24° C., however, the majority of knob was in the soluble fraction. The knob was purified by ammonium sulfate precipitation and anion exchange chromatography, and the his-tag was removed by digestion with thrombin. A sample of purified Ad12 knob, visualized by SDS-PAGE, displayed as a single band at the expected molecular weight. Ad12 knob was then incubated with the his-tagged D1 or D1/D2 in the presence of purified Ad2 hexon protein (included as a specificity control). The mixtures were then adsorbed to Ni-NTA beads to capture the his-tagged CAR fragments. In control incubations lacking the CAR fragments, Ad12 knob and Ad2 hexon both failed to bind to Ni-NTA beads, demonstrated by an absence of bands upon SDS-PAGE analysis of bead eluate. In the presence of either D1 or D1/D2, however, Ad12 knob bound to Ni-NTA beads and could be easily detected in bead eluate by SDS-PAGE analysis, whereas Ad2 hexon did not. This suggested that the CAR IgV domain (D1) specifically binds the Ad12 knob. This conclusion was supported by the results of an experiment to test whether his-tagged Ad12 knob and sD1 form specific complexes. Purified, his-tagged Ad12 knob was mixed with a partially purified preparation of sD1 and incubated briefly to allow protein complexes to form. The mixture was then applied to a column of Ni-NTA beads, unbound proteins were washed from the column, and the bound fraction was eluted with EDTA. SDS-PAGE analysis of the bead eluate revealed the presence of Ad12 knob and sD1, seen as two distinct bands at their expected molecular weights. Thus, D1 alone is sufficient for binding to the Ad12 knob.

Figure 2:
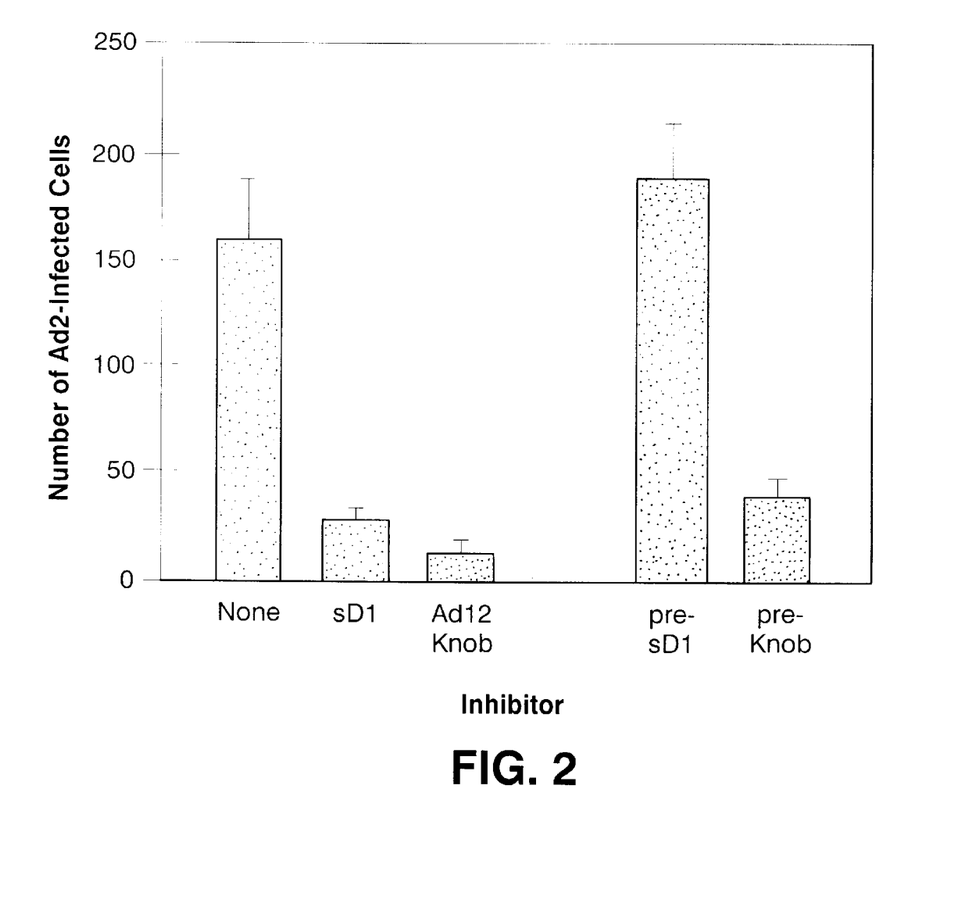
FIG. 2 is a diagrammatic representation of results from experiments measuring the ability of sD1 and Ad12 knob to prevent infection of cells by Ad2. HeLa cell monolayers were infected with about 200 focus-forming units (FFU) per well of Ad2 virus in the presence or absence of sD1 or Ad12 knob. The number of infected cells that resulted is shown (mean±SD). Control cultures were pretreated with sD1 and knob (pre-sD1, pre-Knob) and then washed prior to infection.

To determine if the binding activities of the recombinant Ad12 knob and the CAR IgV domain have the same specificities as their native fiber and CAR counterparts, the ability of Ad12 knob and sD1 to inhibit Ad2 infection of HeLa cells was tested. As shown in FIG. 2, Ad2 infectivity was significantly inhibited when either sD1 or Ad12 knob was included in the virus inoculum during virus adsorption. No inhibition of infection was observed in cell cultures that were pretreated with sD1 and then washed prior to virus adsorption, indicating that the inhibitory activity of sD1 does not result from a cytotoxic effect on cells. Cells similarly pretreated with Ad12 knob, however, were still partially refractory to infection by Ad2 virus. This most likely results from incomplete dissociation of knob from the CAR receptors on cells rather than a cytotoxic effect. Thus, the binding specificity of native fiber and CAR is reconstituted in recombinant Ad12 knob and sD1.

Physical Characteristics of Ad12 Knob and CAR Domains

Figure 3:
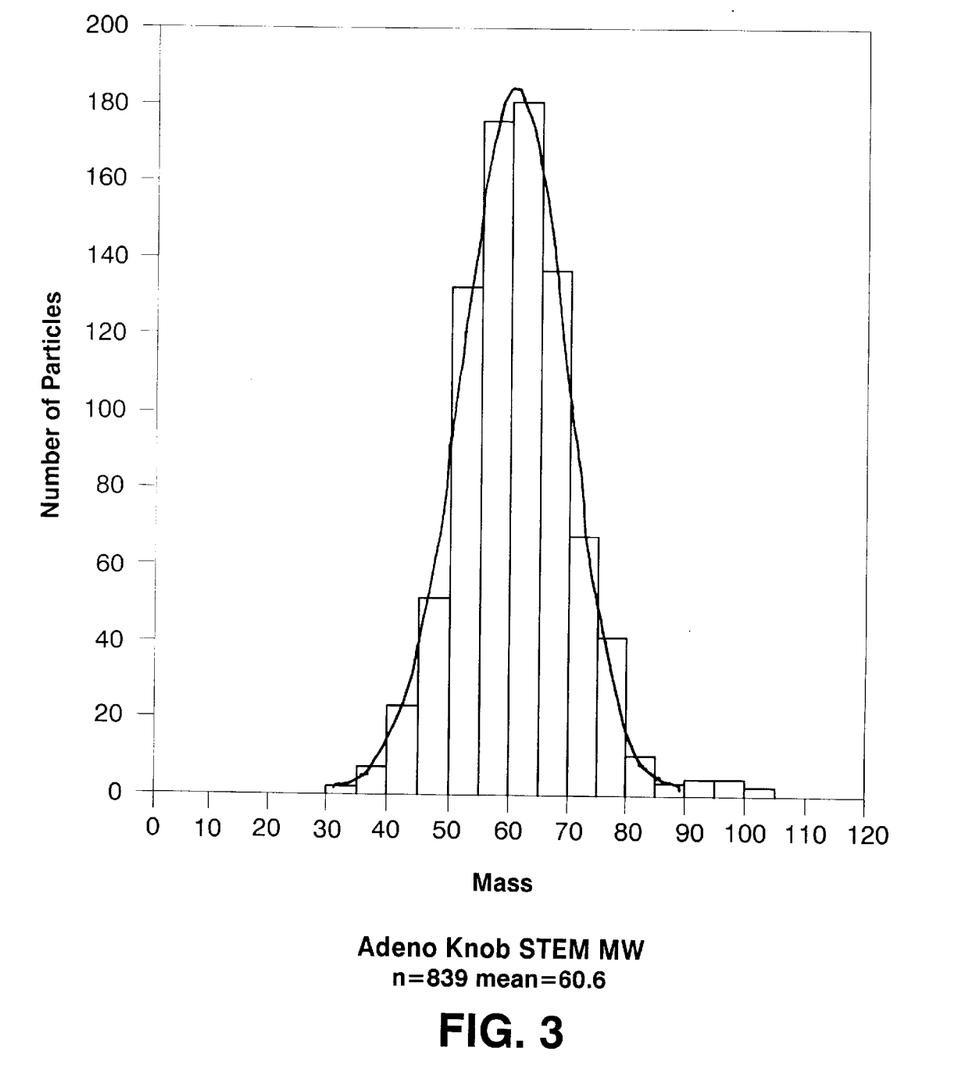
FIG. 3 is a diagrammatic representation of data from scanning transmission electron microscopy (STEM) analysis experiments measuring the mass of Ad12 knob.

Analysis of boiled and untreated samples of Ad12 knob by SDS PAGE showed bands of 20 and 60 kDa, respectively, suggesting that, like the Ad5 fiber knob, the Ad12 knob is trimeric. To confirm this result, a sample of Ad12 knob was examined in the Brookhaven scanning transmission electron microscope (STEM), which measures the mass/unit length of macromolecules. In good agreement with the PAGE results, STEM analysis showed the Ad12 knob has a mass of 60.6 kDa (FIG. 3).

Figure 4:
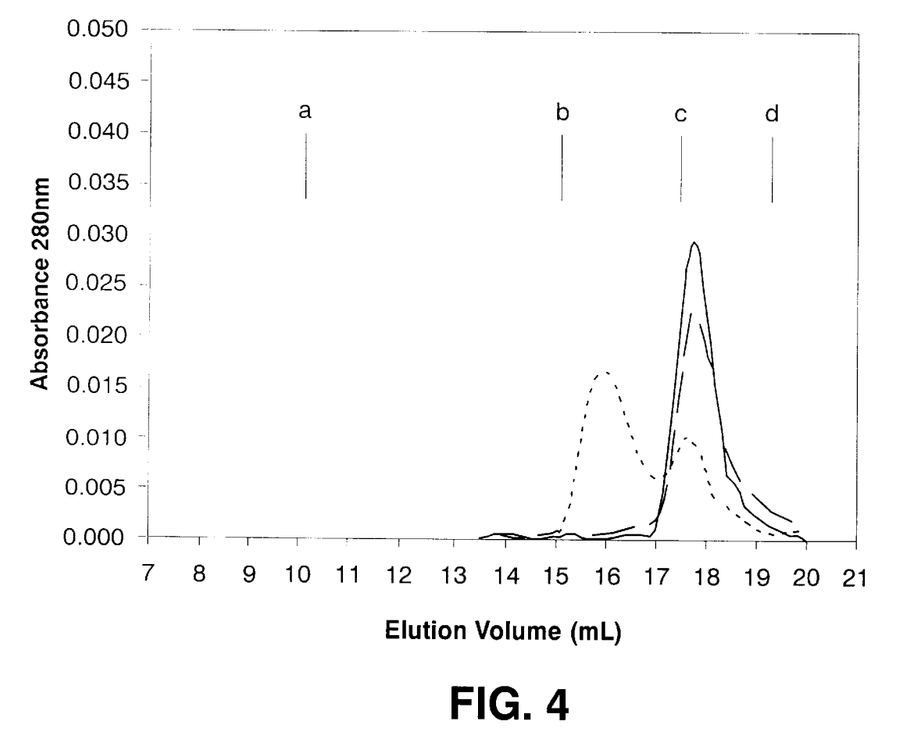
FIG. 4 is a diagrammatic representation of data from size exclusion chromatography of knob, CAR domains and knob-CAR complex. 20 µL aliquots of purified 41.7 µM CAR D1/D2 (), 40.7 µM Ad12 knob ( - - - ), or a mixture containing 32.4 µM knob and 30 µM D1/D2 ( . . . ) were chromatographed on a Superose 6 gel filtration column at a flow rate of 0.25 mL/min (all of the concentrations given refer to the monomeric species). The marks show the elution position of size markers: a, earthworm hemoglobin (3.8 MDa); b, dodecameric earthworm hemoglobin (200 kDa); c, bovine serum albumin (67 kDa); and d, cytochrome c (12 kDa).

The Ad12 knob and the refolded D1 and D1/D2 CAR domains were subjected to gel filtration chromatography to determine their native sizes (FIG. 4). In all three cases, the proteins eluted as symmetric peaks in an elution volume that was independent of the protein concentration (1–500 µM monomer). D1 consistently eluted as a ~30 kDa species while both D1/D2 and knob eluted as ~60 kDa species. Based upon the primary amino acid sequences of these proteins, the gel filtration data suggest that both D1 and D1/D2 are dimers while Ad-12 knob is a trimer. When D1/D2 and knob were mixed together at equimolar (monomer:monomer) ratios two peaks were observed in the elution profiles, a low molecular weight species eluting at a position corresponding to free Ad12 knob or D1/D2 and a higher molecular weight species eluting at a molecular mass of 100 kDa. Fractions from the two peaks were analyzed by SDS-PAGE, which revealed that the high molecular weight peak corresponded to the knob-D1/D2 complex, while the lower molecular weight species was free D1/D2. Similar results were observed for complexes of knob and D1, which eluted at ~80 kDa.

Methods of the Invention

Expression and Purification of Ad12 Knob. A DNA fragment encoding the entire Ad12 fiber knob domain and several flanking amino acids from the fiber shaft (amino acids 401–587) (corresponding to nucleotides 30571–31128 of GenBank Accession #X73487) was amplified from viral DNA by PCR (30 cycles of 94° C./30 sec, 55° C./40 sec, 72° C./60 sec) using primers #1, CATATGAGCAACACTCCATACG, (SEQ ID NO:2) and #2, GGATCCTTATTCTTGGGTAATGT, (SEQ ID NO:3) (FIG. 1a). The resulting PCR product was cloned between the NdeI and BamHI sites of pET15b (Novagen) and transformed into strain BL21-DE3 (Novagen) for protein expression. Overnight cultures grown in LB broth containing 150 mg/L penicillin G (Sigma) were diluted 100-fold into fresh LB-penicillin broth and grown at 37° C. until midlog phase (OD of 0.8 at 600 nm) at which time they were chilled to 24° C. and adjusted to 50 µM IPTG (isopropyl β-D thiogalactopyranoside) to induce knob expression. After shaking (250 rpm) overnight at 24° C., the cells were collected by centrifugation, resuspended in 10% of the original culture volume of STE (10 mM Tris-HCl pH 8.0, 100 mM NaCl, 1 mM EDTA (ethylenediaminetetraacetic acid)) containing 100 µg/ml lysozyme, and subjected to 3 cycles of freezing and thawing. The viscous cell lysate was then sonicated and cleared by centrifugation at 25,000×g for 10 min. Knob was precipitated from the supernatant by addition of solid ammonium sulfate to 35% saturation (25° C.), dialyzed against several changes of 10 mM Tris-HCl (pH 7.5) and passed over a column of DEAE-cellulose (DE52, Whatman) equilibrated in the same buffer. Knob was recovered from the flow-through fractions essentially free of contaminating *E. coli* proteins and nucleic acids, and was further purified by Ni-NTA affinity chromatography according to the manufacturer's instructions (Qiagen). About 100 mg of purified Ad12 knob was obtained from one liter of bacterial culture.

Expression and Purification of CAR Protein Fragments. cDNA fragments encoding the human CAR extracellular domains (D1 and D1/D2, FIG. 1b) were amplified by RT-PCR of total RNA from a mouse A9 cell line transformed with multiple copies of the cloned human CAR gene. First strand cDNA synthesis was primed by oligo-dT. Primers #3: CCATGGGTATCACTACTCCTGAAGAGA (SEQ ID NO:4) (the first 6 nucleotides add two upstream codons, encoding M20 and G21. The remaining nucleotides correspond to nucleotides 121–141 of GenBank Accession #Y07593), #4:CTCGAGCGCACCTGAAGGCTTA (SEQ ID NO:5) (complementary to GenBank Accession #Y07593 nucleotides 476–491) #5:CTCGAGTGAAGGAGGGA-CAAC (complementary to GenBank Accession #Y07593 nucleotides 744–758) (FIG. 1b) were designed for cloning D1- and D1/D2-encoding PCR products between the NcoI and XhoI sites of expression vector pET20b (Novagen). The PCR cycling program was identical to that used for Ad12 knob. These same PCR products were also cloned into pET15b as NcoI-XhoI restriction fragments, and thus lacked the vector-encoded hexahistidine tag, and each had an additional 22 amino acid-long carboxy-terminal extension encoded by vector sequences downstream of the XhoI site (FIG. 1c). Another set of primers (#6–#8, FIG. 1b) was designed to adapt the CAR PCR products for cloning between the pET15b NdeI and BamHI restriction sites, which provides for attachment of the amino-terminal hexahistidine tag to the expressed proteins. Primer #6:CATATGGGTATCACTACTC (SEQ ID NO:7) (the first 7 nucleotides add two upstream codons, encoding M20 and G21. The remaining nucleotides correspond to nucleotides 121–132 of GenBank Accession #Y07593), #7: GGATCCTACGCACCTGAAGGCT (SEQ ID NO:8) (complementary to nucleotides 478–493 of GenBank Accession #Y07593) and #8: GGATCCTATCCAGCTTTATTTGAAG (SEQ ID NO:9) (complementary to nucleotides 754–770 of GenBank Accession #Y07593). Stop codons were built into the reverse primers to avoid synthesis of the CAR fragments with the vector-encoded carboxy-terminal extensions.

The procedure used for expression of the initial pET15b-D1 construct (PCR product from primers #3 and #4) was similar to that described above for Ad12 knob except that the culture was induced at 18° C. Soluble D1 (sD1), produced from the pET15b NcoI/XhoI construct, was precipitated from cleared cell lysates by ammonium sulfate precipitation (35–60% cut, 25° C.) and was partially purified by anion exchange chromatography (DE52) in 10 mM Tris-HCl buffer (pH 7.5). About 5 mg of partially purified sD1 was recovered from one liter of bacterial culture. The hexahistidine-tagged CAR fragments expressed from the second set of pET15b constructs (using primers #6–#8, FIG. 1b) were insoluble, but were recovered from inclusion bodies. Cultures were induced at 37° C., and cleared lysates were prepared as described above. After centrifugation, the supernatant was discarded, the pellet was washed several times in STE containing 0.1% NP40, dissolved in 8 M urea/50 mM β-mercaptoethanol/50 mM Tris-HCl (pH 9.2) (20 ml per liter of initial culture), and then diluted with 15 volumes of 20 mM Tris-HCl (pH 8.0). The slightly hazy solution was passed through a 10 ml bed volume of DEAE-Sepharose Fast Flow (Pharmacia) equilibrated in 20 mM Tris-HCl (pH 8.0). Approximately half of the bound CAR fragments eluted with 50 mM NaCl and were essentially pure. The remaining bound CAR eluted with 300 mM NaCl along with contaminating *E. coli* proteins, and was discarded.

Export of CAR D1 and D1/D2 into the *E. Coli* Periplasm. Mid-log phase cultures of strain BL21-DE3 cells transformed with pET20b-D1 and pET20b-D1/D2 were treated with IPTG to induce synthesis of D1 and D1/D2. After 3 hr of induction, whole cell lysates were prepared and analyzed by SDS-PAGE.

D1 and D1/D2 expression and solubility in the *E. Coli* cytoplasm. BL21-DE3 cells transformed with pET15b-D1 and pET15b-D1/D2 (PCR products from reactions with primers 3–5, FIG. 1b) were induced with IPTG at 18° C. Protein content of whole cell lysates and of the soluble and insoluble fractions of cell sonicates were analyzed by SDS-PAGE.

Assays for Detection of knob-CAR Complexes. The hexahistidine tag was cleaved from Ad12 knob using biotinylated thrombin and was then passed through Ni-NTA and avidin columns to remove residual his-tagged proteins and thrombin. The resulting knob was mixed with purified Ad2 hexon protein and then divided into 3 equal samples. His-tagged D1 or D1/D2 were then added to 2 of the samples, and an equivalent volume of buffer added to the third (control) sample. Each sample was then batch-adsorbed to Ni-NTA beads, washed, and eluted with 100 mM EDTA/25 mM Tris-HCl (pH 8.0). Samples were then electrophoresed in SDS-polyacrylamide gels and stained with coomassie blue.

Inhibition of Ad2 Infection of HeLa Cells. HeLa monolayer cultures were grown in 50% Dulbecco's modified Eagle medium (DMEM, Gibco)/50% Ham's F12 Nutrient Mixture (Gibco) containing 10% calf serum. Monolayers were seeded in 24-well cluster plates 1 day before infection. Ad2 virus diluted in binding buffer (50% DMEM, 50% PBS, 0.4% bovine serum albumin) was divided into 3 equal samples and mixed with an equal volume of Ad12 knob, sD1 (both approximately 2 mg/ml in PBS) or an equal volume of binding buffer. Each preparation was adsorbed in triplicate (0.2 ml/well) for 30 min at 4° C., the wells were then washed twice with PBS and incubated for 2 days at 37° C. in DMEM containing 2% calf serum. The number of infected cells in each culture was then determined by immunoassay for the viral hexon antigen as previously described (Bai, et al., *J. Virol*. 67: 5198–5205 (1993)). To control for possible cytotoxic effects of the recombinant proteins, additional sets of cultures were pre-incubated with Ad12 knob or sD1 (1 mg/ml) in binding buffer for 30 min, washed twice with PBS and then infected with Ad2 virus.

Analysis of Ad12 Knob by Scannina Transmission Electron Microscopy (STEM). The mass of Ad12 knob (with the His tag removed) was measured by STEM. Five microliters of the purified protein (~10 mG/ml) was applied to an electron microscope holey grid covered with thin (~2 nm) carbon, and after 1 minute was wicked and washed 10 times with 20 mM ammonium acetate. The grid was blotted and rapidly frozen in liquid nitrogen slush, then freeze-dried overnight. Data was collected with the Brookhaven NIH Biotechnology Resource STEM (Wall, J. S. (1982) in *Introduction to Analytical Electron Microscopy*, Plenum, N.Y., p 333–342) at scans of 0.512 micron width with a dose of 200 electrons/$nm^2$. Protein particle masses were measured (Wall, et al., *Annu. Rev. Biophys. Biophys. Chem*. 15: 355 (1986)) off-line using the "PC-Mass" program, and statistics and curve fitting were generated with SigmaPlot. Mass calibration was done using TMV particles adhered to the grid before the sample was applied.

Gel Filtration Analysis of Ad12 Knob and CAR D1 and D1/D2.

The native molecular masses of Ad12 knob, the refolded D1 and D1/D2 domains of CAR, and knob complexed to D1 or D1/D2 were determined by size exclusion chromatography using a Superose 6 gel permeation column. In brief, 20 μL aliquots of purified proteins or protein complexes were chromatographed at 0.25 ml/min on the Superose 6 column in 20 mM Tris-HCl pH 7.8, 200 mM NaCl, 1 mM DTT and 0.1 mM EDTA. Aliquots of the fractions were analyzed by SDS-PAGE. These experiments were run over a range of concentrations from 1–500 μM monomer.

What is claimed is:

1. An isolated polypeptide consisting essentially of an amino acid sequence which corresponds to adenovirus binding domain D1 of human CAR (coxsackievirus and adenovirus receptor) protein.

2. The isolated polypeptide of claim 1 wherein the amino acid sequence corresponds to residues 20–144 of human pre-CAR protein with the exception of two amino acid substitutions, L20M and S21G.

3. The isolated polypeptide of claim 1 wherein the amino acid sequence corresponds to residues 20–144 of human pre-CAR protein.

4. An isolated polypeptide consisting essentially of an amino acid sequence which corresponds to extracellular domains D1 and D2 of human CAR (coxsackievirus and adenovirus receptor) protein wherein the amino acid sequence corresponds to residues 20–237 of human pre-CAR protein with the exception of two amino acid substitutions, L20M and S21G.

5. An isolated fusion protein comprising a first amino acid sequence which corresponds to amino acids 20–144 of human pre-CAR protein (D1) fused in frame to a second amino acid sequence comprising LEDPAANKARKEAELAAATAEQ (SEQ ID NO:1)
wherein the second amino acid sequence facilitates folding of D1 into a functional, soluble domain when expressed in bacteria, the second amino acid sequence being located C-termninal to the first amino acid sequence.

6. An isolated polypeptide consisting essentially of an amino acid sequence which corresponds to extracellular domains D1 and D2 of human CAR (coxsackievirus and adenovirus receptor) protein wherein the amino acid sequence corresponds to residues 20–237 of human pre-CAR protein.

* * * * *